United States Patent [19]

Brain

[11] Patent Number: 5,303,697
[45] Date of Patent: Apr. 19, 1994

[54] ARTIFICIAL AIRWAY DEVICE

[76] Inventor: Archibald I. J. Brain, The Studio, St. Andrews, Abney Court Drive, Bourne End, Bucks SL8 5DL, United Kingdom

[21] Appl. No.: 869,491
[22] PCT Filed: Feb. 11, 1992
[86] PCT No.: PCT/GB92/00242
§ 371 Date: Apr. 20, 1992
§ 102(e) Date: Apr. 20, 1992

[30] Foreign Application Priority Data

Feb. 11, 1991 [GB] United Kingdom ............ 9102821

[51] Int. Cl.⁵ ..................... A61M 16/00; A61B 1/26
[52] U.S. Cl. ..................... 128/200.26; 128/207.14; 128/207.15
[58] Field of Search ......... 128/32, 4, 5, 6, 11, 128/12, 15, 17, 898, 200.24, 200.26, 207.14, 207.19, 207.18, DIG. 26; 604/96

[56] References Cited

U.S. PATENT DOCUMENTS

| 3,225,767 | 12/1965 | Smith | 128/200.26 |
|---|---|---|---|
| 4,054,135 | 10/1977 | Berman | 128/200.26 |
| 4,211,234 | 7/1980 | Fisher | 128/200.26 |
| 4,304,228 | 12/1981 | Depel | 128/200.26 |
| 4,306,547 | 12/1981 | Lowell | 128/11 |
| 4,351,330 | 9/1982 | Scarberry | 128/207.15 |
| 4,449,526 | 5/1984 | Elam | 128/206.24 |
| 4,553,540 | 11/1985 | Straith | 128/200.26 |
| 4,852,565 | 8/1989 | Eisele | 128/207.14 |
| 4,919,126 | 4/1990 | Baildon | 128/207.14 |
| 4,982,729 | 1/1991 | Wu | 128/11 |
| 5,033,466 | 7/1991 | Weymuller | 128/207.15 |
| 5,038,766 | 8/1991 | Parker | 128/200.26 |
| 5,174,283 | 12/1992 | Parker | 128/200.26 |

FOREIGN PATENT DOCUMENTS

| 0110333 | 6/1984 | European Pat. Off. . |
|---|---|---|
| 0389272 | 9/1990 | European Pat. Off. . |
| 2517974 | 6/1983 | France . |
| 445218 | 4/1936 | United Kingdom ........... 128/200.26 |
| 2137096 | 10/1984 | United Kingdom . |
| 2229367 | 9/1990 | United Kingdom ........... 128/207.15 |

*Primary Examiner*—Edgar S. Burr
*Assistant Examiner*—Eric P. Raciti
*Attorney, Agent, or Firm*—Hopgood, Calimafde, Kalil, Blaustein & Judlowe

[57] ABSTRACT

An artificial airway device to facilitate lung ventilation in an unconscious patient comprises a rigid airway tube (10), which is curved to follow the airway of the patient, opening into the interior space or lumen of a mask portion (12) whose periphery (14) is adapted to seal around the inlet (36) to the larynx (38), and a rigid handle (9) mounted at the outer end of the airway tube (10) and curved away from the mouth of the airway tube (10).

11 Claims, 3 Drawing Sheets

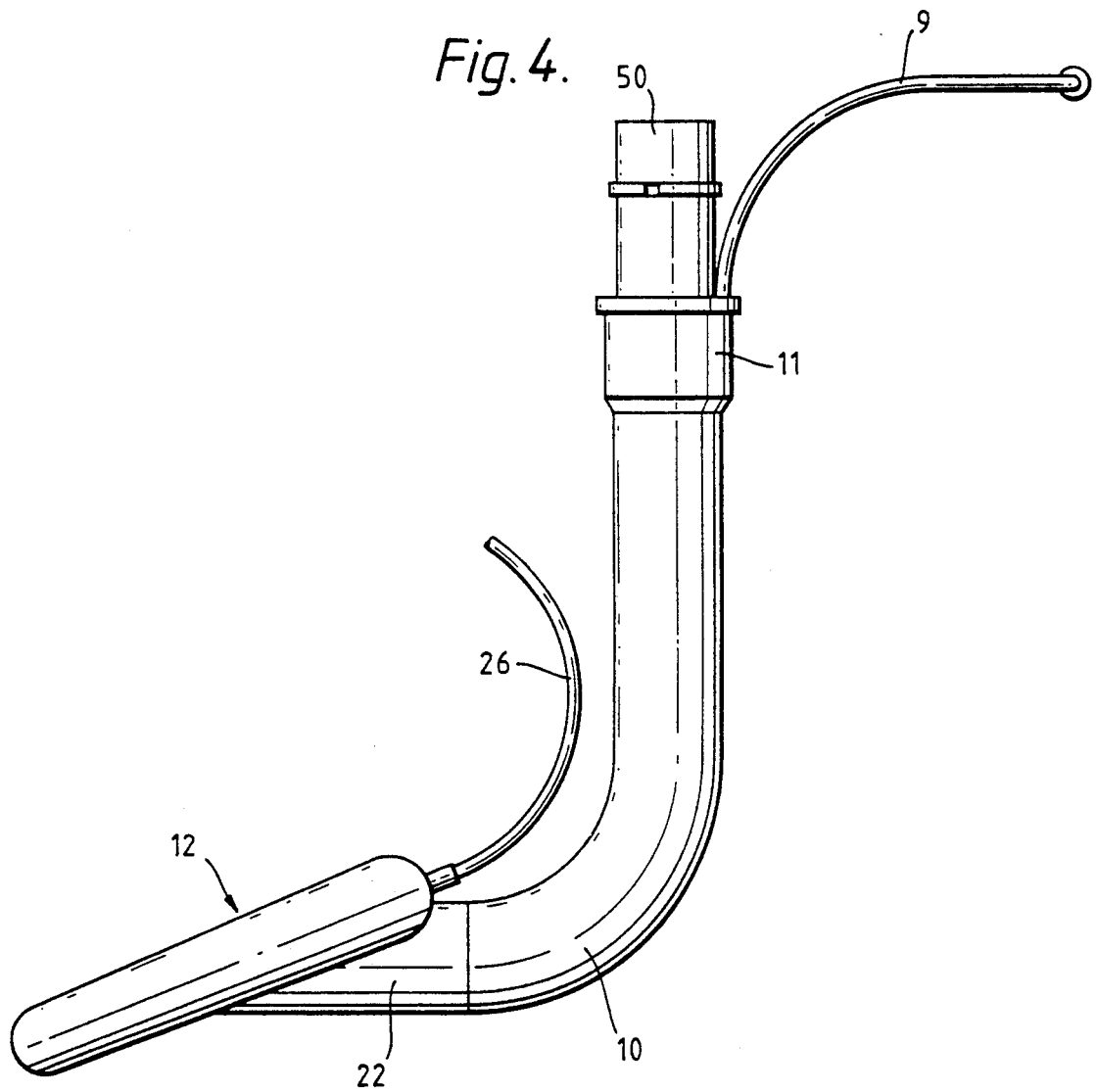

ARTIFICIAL AIRWAY DEVICE

FIELD OF THE INVENTION

The present invention relates to an artificial airway device of the type capable of facilitating ventilation in unconscious patients, and more specifically to such a device designed for placing in the oropharynx of the patient in order to prevent airway obstruction and to permit ventilation.

BACKGROUND TO THE INVENTION

British Patent Publications Nos. 2 111 394 A and 2 229 367 A describe artificial airway devices capable of facilitating lung ventilation in an unconscious patient, referred to hereinafter as "laryngeal masks". The insertion of a laryngeal mask needs to be undertaken by persons practised in the use of the mask and is not so effective in emergency situations where untrained personnel may be called to a patient. Furthermore, these devices suffer from the limitation that they do not offer the same degree of protection against aspiration of regurgitated gastric contents into the lungs as does an endotracheal tube. The latter device has long been established as the most reliable means of preventing such aspiration in the unconscious patient and consists of a tube with an inflatable cuff, inflation of which forms a seal against the wall of the trachea. The laryngeal mask by contrast forms a seal around the perimeter of the larynx by means of an inflatable elliptical cuff. The seal so formed depends on pressure against muscular structures which may by their contraction or relaxation Hence, the degree of protection against aspiration already afforded by the laryngeal mask would be enhanced by allowing intubation with an endotracheal tube, with the laryngeal mask in place. Attempts have been made to intubate through the airway tube of a conventional laryngeal mask and this has been found to be effective. However, only a small diameter endotracheal tube can be passed through the mask. Moreover, as the airway tube is flexible, the operation is awkward and not entirely suited to emergency procedures.

SUMMARY OF THE INVENTION

According to one aspect of the present invention, there is provided an artificial airway device to facilitate lung ventilation in an unconscious patient, comprising a substantially rigid airway tube and a mask attached to an end of the airway tube, the mask having an annular peripheral formation of roughly elliptical shape capable of conforming to, or readily fitting within, the actual and potential space behind the larynx so as to form a seal around the circumference of the laryngeal inlet without the device penetrating into the interior of the larynx, the annular peripheral formation surrounding a hollow interior space or lumen of the mask into which the airway tube opens, in which said airway tube is curved to follow the airway of a patient, and said device further comprises a substantially rigid handle portion mounted to an end of the airway tube remote from the mask and extending in a direction away from the mouth of said airway tube.

In the preferred embodiment, the handle portion curves in a direction opposite to the direction of curvature of the airway tube, for example to form an S shape. This shape allows a person to insert a laryngeal mask into a patient quickly and effectively.

The handle portion can be removably mounted to the airway tube so that it can be detached after being used to guide the laryngeal mask into place. This has the advantage that the mask can be left in place in a patient without impeding medical attention.

The mask may include a stiff back piece surrounded by the annular peripheral portion. This assists in allowing the larynx to be pulled forward by manipulating the handle portion to enable regurgitated stomach contents to be released and to increase the seal of the annular peripheral formation against the laryngeal inlet.

The diameter of the airway tube can be such as to allow an endotracheal tube to be inserted through the tube to intubate a patient while the handle portion is braced manually. The inventor has found that in this way it is possible to use a laryngeal mask as a guiding tool to facilitate passage of a normal diameter endotracheal tube into the trachea. This is feasible because the aperture in the laryngeal mask when correctly in position faces directly into the laryngeal orifice. By passing a well lubricated endotracheal tube and cuff through the tube of the laryngeal mask, it is thus possible to perform blind intubation whilst still ventilating the unconscious patient through the laryngeal mask.

The end of the airway tube remote from the mask may comprise a connecting portion for connection of the airway tube to a ventilation apparatus. This can enable a patient to be ventilated with or without intubation.

The device may include a bite portion adjacent the end of the airway tube remote from the mask for protecting the teeth of the patient.

The airway tube and the handle portion may be of stainless steel.

BRIEF DESCRIPTION OF THE DRAWINGS

FIG. 4 shows an alternative laryngeal mask airway according to the present invention.

DESCRIPTION OF THE PREFERRED EMBODIMENTS

Specific embodiments of the present invention will now be described by way of example with reference to the accompanying drawings.

Figure 1:
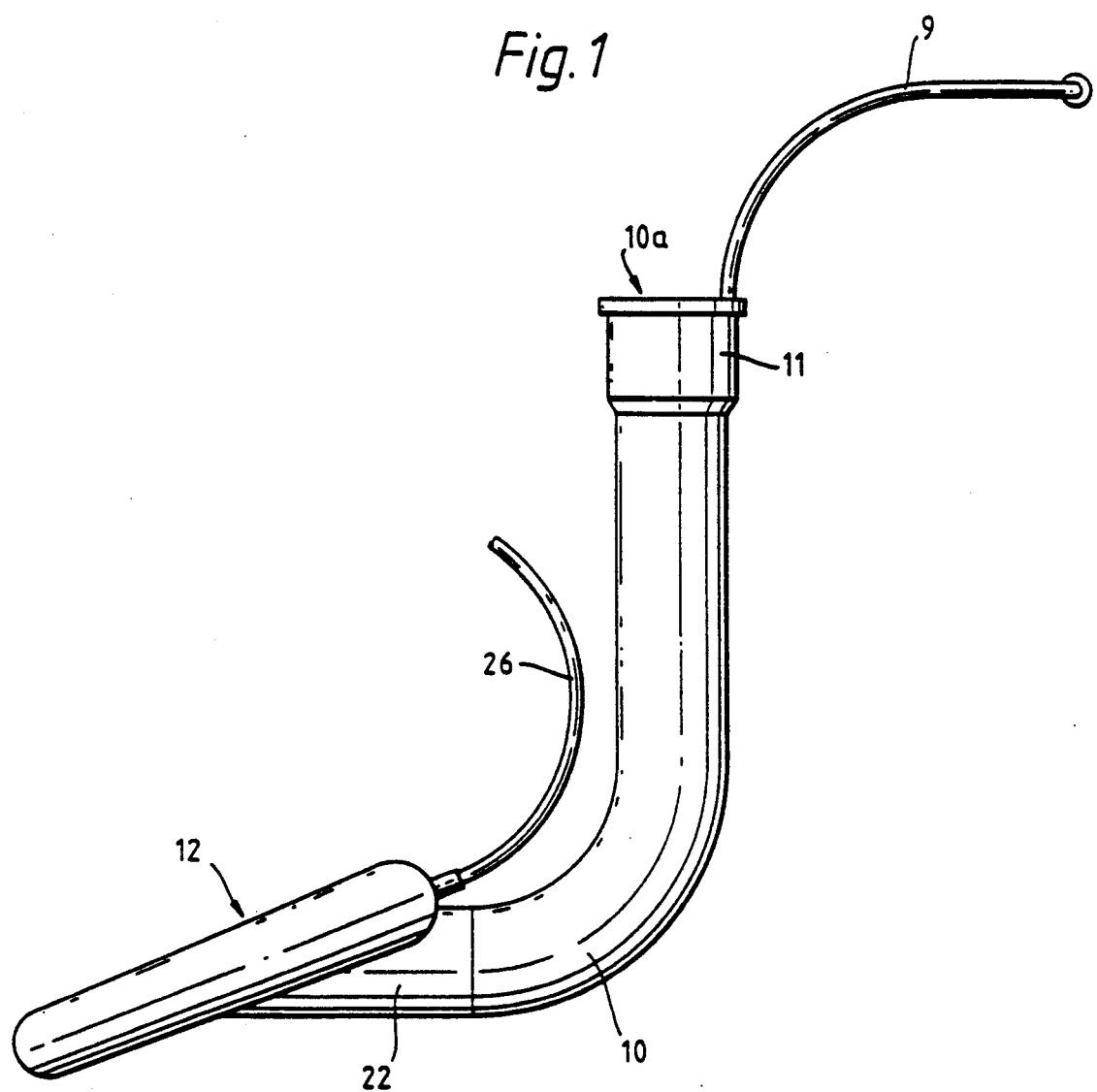
FIG. 1 shows a laryngeal mask airway according to an embodiment of the present invention.

FIG. 1 shows a laryngeal mask 12 made of silicone and mounted to a stainless steel airway tube 10. The airway tube 10 is bonded by means such as ribbing and/or adhesives to a breathing tube port 22 of the laryngeal mask 12. The laryngeal mask is known per se from GB 2111394 and 2229367 the contents of which are incorporated herein by reference. Only those aspects of the mask required to explain the present invention are described herein. The airway 10 is of sufficient diameter to accommodate an 8 mm cuffed endotracheal tube. The airway tube 10 is bent around a curve having a curvature angle of approximately 90° in such a way as to fit around the curvature at the back of the tongue. At its outer end 10a the tube widens and incorporates a flange 11 made of a material which will withstand biting without being hard enough to damage the patient's teeth. A handle 9 is securely mounted to the outer end 10a of the tube 10, the handle 9 being curved in the opposite direction to the tube 10. The handle 9 can be fixed to the airway tube 10 or it can be removably mounted thereto.

Figure 2:
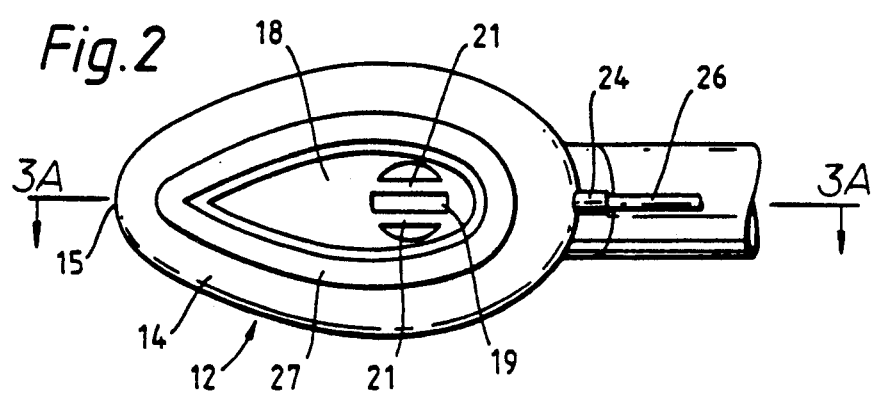
FIG. 2 shows a plan view of the laryngeal mask portion of the embodiment shown in FIG. 1.

FIG. 2 shows details of the laryngeal mask 12 in plan view.

Figure 3:
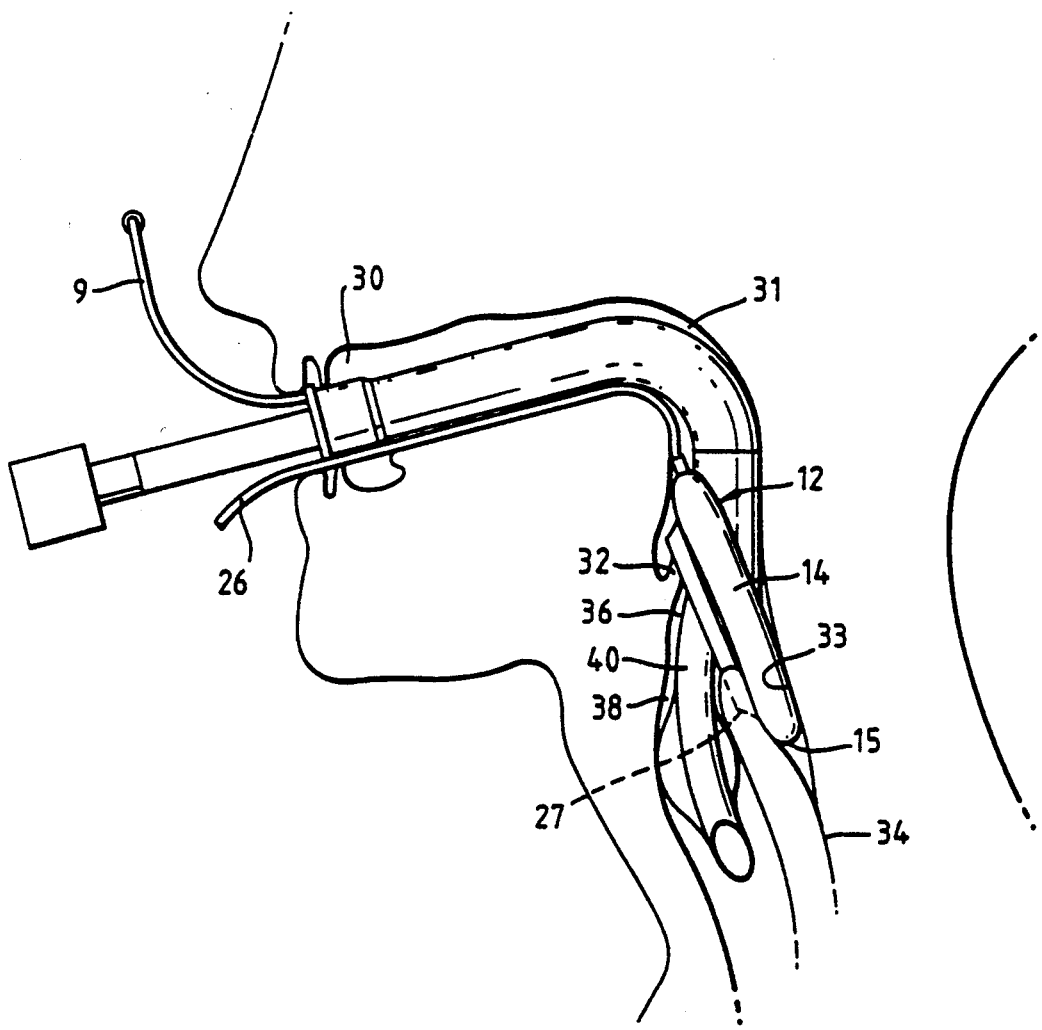
FIG. 3 shows a laryngeal mask according to an embodiment of the present invention in use in a patient.

The mask 12 is of flexible rubber sheet material having an inflatable tubular ring 14 of the same silicone rubber material forming its periphery. The peripheral ring 14 is roughly elliptical in plan although its distal end 15 may be slightly elongated to conform with the triangular shape of the base of the hypopharynx where it becomes continuous with the upper end of the oesophagus 34 (FIG. 3). The peripheral ring 14 includes a port 24 for connection to a rubber tube 26 of narrow diameter, through which the peripheral ring 14 may be inflated.

The breathing tube port 22 opens into an aperture 19 in the mask, which is provided with cross-bars 21 extending across the aperture, which prevents the epiglottis from falling into the aperture and obstructing the airway. The aperture 19 opens into a lumen 18 or hollow interior of the mask. The lumen 18 is surrounded by a soft flexible upstanding collar 27, of flexible sheet rubber material, adhered at its base to the peripheral ring 14 so that its free end extends away from the lumen 18 of the mask.

Figure 3A:
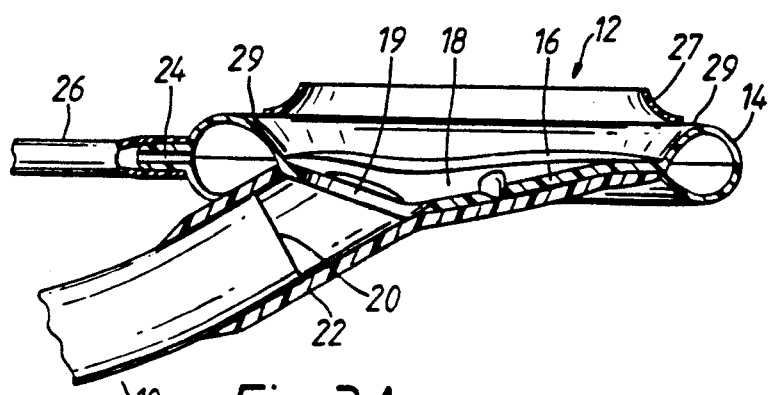
FIG. 3A is a sectional view taken along the line 3A—3A of FIG. 2.

The breathing-tube port 22 may, as in the case of said GB 2,229,367 and as shown in FIG. 3A, be a short piece of thick-walled silicone-rubber tubing, the other end of which is moulded to fit against the outer edge of web 16 and around the aperture 19, so as to form a backpiece for the mask, which backpiece carries the airway tube 10 at an angle of substantially 30° to the plane of the ring 14. Thus, the lumen 18 is enclosed at the back of the mask by a back-piece which can be made of relatively stiff material such as a high-grade silicone.

To insert the laryngeal mask airway, the peripheral ring 14 is fully deflated and the device is inserted by means of the handle 9 through the patient's mouth 30 and through the throat 31 past the epiglottis 32 until the mask 12 comes to rest in the position shown in FIG. 3 with the distal end 15 of the ring 14 in the base 33 of the throat. The ring 14 is then inflated to increase the sealing pressure around the inlet 36 to the larynx 38.

Intubation is then formed by passing a standard 8 mm cuffed endotracheal tube 40 through the airway tube 10 and the aperture 19 into the larynx 38. The device is braced against the insertion of the endotracheal tube 40 by means of the handle 12. This enables insertion to be done blindly (i.e. without a laryngoscope). It thus makes the mask ideally suited to emergency conditions.

The breathing tube port 22 opens into the lumen 18 of the mask at the appropriate angle for guiding the endotracheal tube 40 into the larynx 48, thereby allowing blind intubation of the larynx 38. However, in a situation where the endotracheal tube does not pass into the larynx at the correct angle, the position of the mask 12 may be controlled by means of the handle 11 so that the correct angle of intubation is achieved.

The handle 9 also allows the mask 12 to be pulled forwards towards the larynx 38, thereby pulling the larynx 38 forwards to allow regurgitated stomach contents to be released while maintaining a tight seal around the inlet 36 of the larynx 38.

In an alternative embodiment of the present invention shown in FIG. 4, a standard connector 50 is provided at the outer end of the airway tube 10 for attachment of conventional anaesthetic hosing and ventilation apparatus.

Thus, embodiments of the present invention enable blind intubation through a modified laryngeal mask with a tube such that:

a) The position of the laryngeal mask against the laryngeal orifice can be influenced by manipulation of a handle attached to the outer end of a rigid tube.

b) The device can be positioned in the patient's pharynx using one hand only for insertion. This has advantages in the emergency situation where a patient may be trapped, for example in a crushed vehicle, making access difficult.

c) The length of the airway tube can be comparatively short to facilitate the passing of a standard endotracheal tube, because of the addition of a handle for controlling the laryngeal mask airway.

d) The airway tube is wide enough to accommodate an endotracheal tube of required diameter.

While the handle 9 and airway tube 10 are of stainless steel in the above embodiments, any rigid sterilisable material may alternatively be used.

Reference herein to actual and potential space behind the larynx will be understood to refer to the space normally available and that which can be become available on flexure of the surrounding structures.

I claim:

1. An artificial airway device to facilitate lung ventilation in an unconscious patient, comprising a substantially rigid airway tube and a mask attached to an end of the airway tube, said mask having a relatively stiff backpiece with an airway-tube portion secured to said substantially rigid airway tube, said mask also having an inflatable annular peripheral formation of roughly elliptical shape capable of conforming to, or readily fitting within, the actual and potential space behind the larynx so as to form a seal around the circumference of the laryngeal inlet without the device penetrating into the interior of the larynx, the annular peripheral formation surrounding a hollow interior space or lumen of the mask into which the airway-tube portion opens, said substantially rigid airway tube being curved to follow the airway of a patient, and said device further comprising a substantially rigid handle portion mounted to an end of the airway tube remote from the mask and extending in a direction away from the curve of said airway tube.

2. An artificial airway device according to claim 1, wherein the handle portion curves in a direction opposite to the curvature of the airway tube.

3. An artificial airway device according to claim 1, in which the annular peripheral formation carries a soft, flexible, upstanding collar surrounding the lumen of the mask so as to improve the sealing contact with the tissues around the circumference of the laryngeal inlet.

4. An artificial airway device according to claim 1, in which the end of the airway tube remote from the mask comprises a connecting portion for connection of the airway tube to ventilation apparatus.

5. An artificial airway device according to claim 1, and including a bite portion adjacent the end of the airway tube remote from the mask for protecting the teeth of the patient.

6. An artificial airway device according to claim 1, in which the airway tube and the handle portion are of stainless steel.

7. An artificial airway device according to claim 1, wherein the handle portion is removably mounted to the airway tube.

8. An artificial airway device according to claim 1, in which said back-piece is of a high-grade silicone material.

9. An artificial airway device to facilitate lung ventilation in an unconscious patient, comprising a substantially rigid airway tube curved between proximal and distal ends to follow the airway of a patient, and a mask attached to the distal end of the airway tube, said mask having a relatively stiff body with an airway-tube portion at mask attachment to the airway tube, said body having an inflatable annular peripheral formation of roughly elliptical shape capable of establishing insertional limitation at engagement with the oesophageal inlet and also capable of inflation in conformance with the actual and potential space behind the larynx so as to form a seal around the circumference of the laryngeal inlet without the device penetrating into the interior of the larynx, the inflatable annular peripheral formation surrounding a hollow interior space of the mask into which the airway-tube portion opens, and said device further comprising a substantially rigid handle mounted to the proximal end of the airway tube and extending in a direction away from the direction of the airway tube at the proximal end thereof.

10. An artificial airway device to facilitate lung ventilation in an unconscious patient, comprising a substantially rigid airway tube curved between proximal and distal ends to follow the airway of a patient, and a mask attached to the distal end of the airway tube, said mask having a relatively stiff body with an airway-tube portion at mask attachment to the airway tube, said body having an inflatable annular peripheral formation of roughly elliptical shape capable of establishing insertional limitation at engagement with the oesophageal inlet and also capable of inflation in conformance with the actual and potential space behind the larynx so as to form a seal around the circumference of the laryngeal inlet without the device penetrating into the interior of the larynx, the inflatable annular peripheral formation surrounding a hollow interior space of the mask into which the airway-tube portion opens, the proximal end of said substantially rigid airway tube being exposed externally of the patient when the annular peripheral formation has been inflated to form the seal around the circumference of the laryngeal inlet, whereby the proximal end is exposed for such manipulation of the substantially rigid airway tube as to enable manipulated force application of the inflated formation into enhanced sealing engagement of the laryngeal inlet.

11. An artificial airway device according to claim 10, in which a substantially rigid handle is affixed to such proximal end and is exposed externally of the patient to facilitate such manipulated force application.

* * * * *